United States Patent [19]

Alexandrescu

[11] Patent Number: 5,757,884
[45] Date of Patent: May 26, 1998

[54] X-RAY DIAGNOSTIC INSTALLATION WITH A SOLID-STATE IMAGE TRANSDUCER

[75] Inventor: Mircea Alexandrescu, Baiersdorf, Germany

[73] Assignee: Siemens Aktiengesellschaft, Munich, Germany

[21] Appl. No.: 804,607

[22] Filed: Feb. 24, 1997

[30] Foreign Application Priority Data

Feb. 23, 1996 [DE] Germany ............... 196 06 873.8

[51] Int. Cl.$^6$ ................................................ H05G 1/64
[52] U.S. Cl. ................... 378/98.7; 378/98.8; 250/378.07
[58] Field of Search ..................... 378/98.7, 98.8, 378/98.3, 97, 108; 250/370.07, 370.11, 370.09

[56] References Cited

U.S. PATENT DOCUMENTS

| | | |
|---|---|---|
| 4,948,966 | 8/1990 | Arques et al. |
| 4,982,418 | 1/1991 | Kuechnel |
| 5,079,426 | 1/1992 | Antonuk et al. ............ 250/370.11 X |
| 5,194,736 | 3/1993 | Meulenbrugge et al. ......... 250/370.07 |
| 5,331,166 | 7/1994 | Yamamoto et al. |
| 5,448,613 | 9/1995 | Haendle et al. |
| 5,523,554 | 6/1996 | Hassler et al. ............ 250/370.11 X |
| 5,574,765 | 11/1996 | Hassler et al. |
| 5,668,375 | 9/1997 | Petrick et al. ............ 378/98.8 X |

FOREIGN PATENT DOCUMENTS

| | | |
|---|---|---|
| 21 35 205 | 7/1980 | Germany |
| 40 17 597 | 12/1991 | Germany |

*Primary Examiner*—David P. Porta
*Attorney, Agent, or Firm*—Hill & Simpson

[57] ABSTRACT

An X-ray diagnostic installation has a high-voltage generator for an X-ray tube for generating an X-ray beam, and an X-ray image transducer formed by a scintillator layer, a semiconductor layer with light-sensitive pixel elements arranged in a matrix, and an array of light-sensitive elements arranged in a matrix behind the semiconductor layer in the beam propagation direction. At least a part of the light-sensitive elements in the array acquires the X-ray dose as a detector, to which a measurement transducer is connected for controlling the high-voltage generator. The light-sensitive elements in the array can be light-emitting diodes for resetting residual charges of the pixel elements in the semiconductor by illumination of the image transducer. Individual light-emitting diodes in the array can be connected to the measurement transducer during the X-ray irradiation as a detector for acquiring the X-ray dose and a remainder of the light-sensitive elements in the array or can be small photodiodes arranged in a matrix with the light-emitting diodes.

9 Claims, 3 Drawing Sheets

X-RAY DIAGNOSTIC INSTALLATION WITH A SOLID-STATE IMAGE TRANSDUCER

BACKGROUND OF THE INVENTION

1. Field of the Invention

The present invention is directed to an X-ray diagnostic installation with a high-voltage generator for an X-ray tube for generating an X-ray beam, and an X-ray image transducer with a scintillator layer and a semiconductor layer with light-sensitive pixel elements arranged in a matrix, and with an array of light-sensitive elements arranged in a matrix arranged therebehind in the beam propagation direction.

2. Description of the Prior Art

German OS 21 35 205 discloses an X-ray diagnostic installation with an automatic exposure unit wherein an X-ray dose is acquired over time as it increases during X-ray irradiation of a subject. The radiation emission can thus be shut off after a prescribed value is reached.

In such X-ray diagnostic installations employing an X-ray image intensifier as the image transducer, it is known to arrange an air-filled ionization chamber in front of the X-ray image intensifier as an auxiliary component for making a measurement of this type. The slight current between two electrode plates with a voltage thereacross is directly proportional to the dose rate of the incident, ionizing radiation. The dose is determined by integration of the dose rate. The measuring precision, however, is too low for fluoroscopy doses.

In a solid-state X-ray image transducer, for example an a-Si:H X-ray image detector, the above information is not available until some time after the end of the X-ray pulse because the image detector is fundamentally operated in storage mode. A dose measurement is thus not possible during the current X-ray pulse but only some time after the end thereof.

To address this problem, German OS 44 26 451, corresponding to U.S. Pat. No. 5,574,765, discloses a solid-state image transducer having an electrically non-conductive layer on which an electrode layer applied as a detector on a semiconductor layer with light-sensitive pixel elements arranged in a matrix. This electrode layer forms a capacitor with the pixel elements to which charge is supplied by means of exposure during irradiation. The capacitor is connected to a measurement transducer for acquiring this charge corresponding to the X-ray dose. The desired measured signal is thereby in fact obtained immediately during the current X-ray pulse; however, a specially constructed image transducer is required.

U.S. Pat. No. 4,948,966 discloses a solid-state image transducer wherein two diodes are connected between the row and column lines of the drive circuits with opposite polarities. The photodiodes are operated in a storage mode using their self-capacitance, so that the can be read out sequentially after an exposure. It must be assured for real-time fluoroscopic mode that the readout can ensue fast enough and that image information of successive images do not mix.

For this reason, a reset produced by exposing the matrix ensues between two readout events. The photodiodes are completely discharged as a result thereof and thus are in low-impedance state. Since the exposure cannot ensue line-by-line, a simultaneous, common resetting of the entire array is undertaken.

SUMMARY OF THE INVENTION

An object of the present invention is to provide an X-ray diagnostic installation of the type initially described which employs a solid-state image transducer and which enables a simple, fast and reliable acquisition of the X-ray dose during the X-radiation.

This object is inventively achieved in an X-ray diagnostic installation having a solid-state image transducer wherein at least a part of the light-sensitive elements is driven such that the image transducer is illuminated for resetting residual charges of the pixel elements, while at least the other part acquires the X-ray dose as a detector to which a measurement transducer is connected for the control of the high-voltage generator. Since about 15% of the light converted by the scintillator layer is not absorbed by the semiconductor layer and emerges at the back side thereof, this light can be acquired by the light sensitive elements. This allows the light penetrating the image transducer to be utilized for dose measurement.

Since light-emitting diodes are also photo-sensitive in the same color range in which they emit light, it has proven advantageous for the light-sensitive elements to be light-emitting diodes for resetting residual charges of the pixel elements by illumination of the image transducer, whereby individual light-emitting diodes can be connected to the measurement transducer during the X-ray irradiation as detector for the acquisition of the X-ray dose. As a result, the light-emitting diodes required for resetting after the X-ray pulse and the readout can also acquire the X-ray dose.

It has proven advantageous to provide at least one switch that connects a light-emitting diode to the measurement transducer during the X-ray pulse and connects the light-emitting diode to the other light-emitting diodes for resetting.

Switching of the light-emitting diodes can be eliminated and a better utilization of the light is obtained when some of the light-sensitive elements are light-emitting diodes for resetting residual charges of the pixel elements by illumination of the image transducer, and others are small photodiodes arranged in the matrix of the light-emitting diodes, whereby the photodiodes are connected to the measurement transducer during the X-ray irradiation as detector for acquiring the X-ray dose.

The spacing of the light-emitting diodes relative to one another always remains the same if the photodiodes are arranged in alternation between the light-emitting diodes in the region of a dominant.

A number of light-sensitive elements can be switched in a simple way by connecting a group of light-sensitive elements to the measurement transducer via a switch during the X-ray pulse, and connecting the light sensitive elements to the remaining light-sensitive elements via the switch for resetting.

An arbitrary dominant can be selected when a number of switches are provided with which the light-sensitive elements can be arbitrarily individually connected to the measurement transducer so as to form a dominant of any desired shape.

A desired dominant can be selected when a number of switchable groups are provided whose arrangements respectfully form the shapes of desired, possible dominants. The appropriate connected group is then selected which has the desired dominant shape.

It has proven advantageous when the solid-state image transducer is an a-Si:H detector.

DESCRIPTION OF THE PREFERRED EMBODIMENTS

Figure 1:
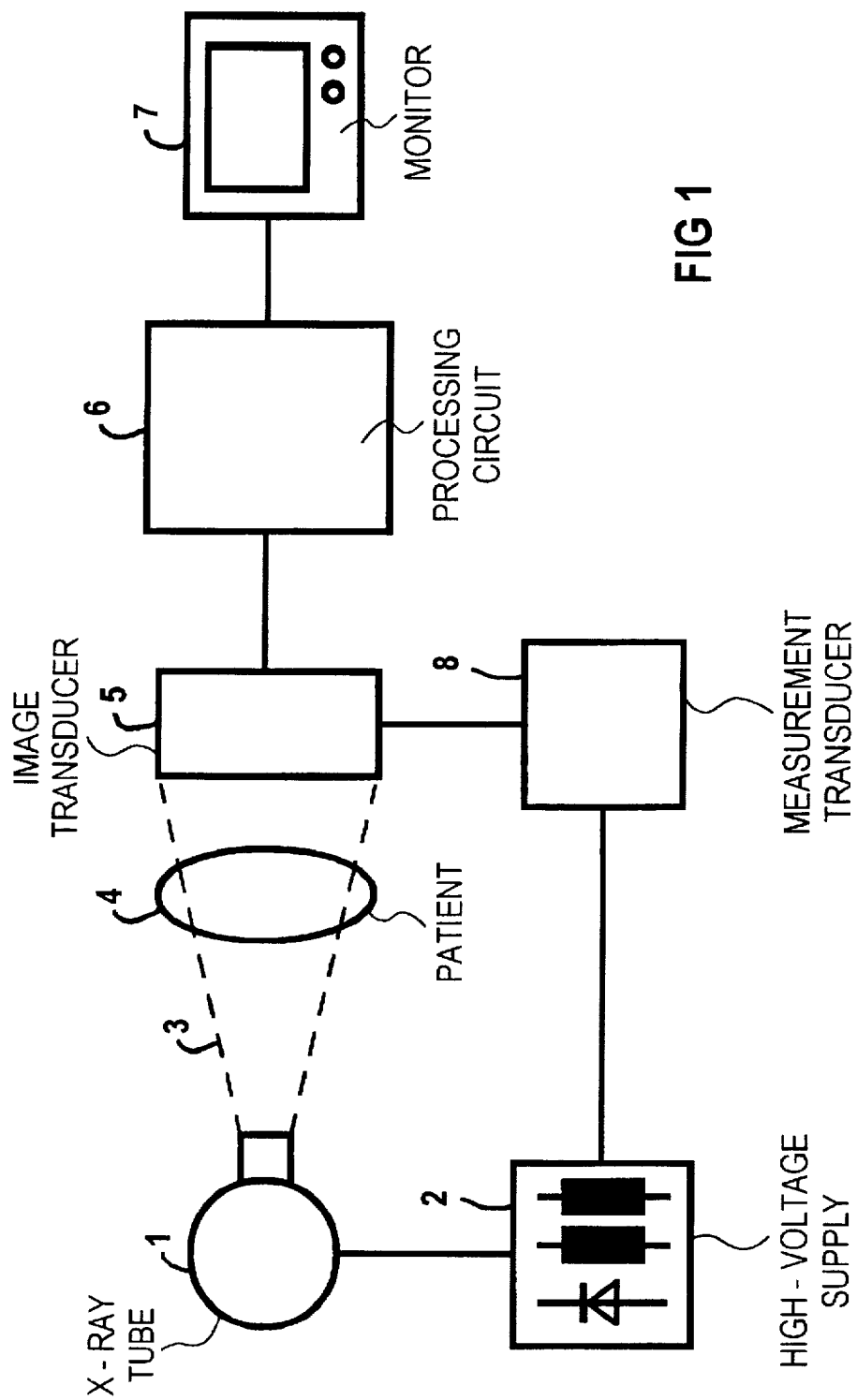
FIG. 1 is a block diagram of an inventive X-ray diagnostic installation.

FIG. 1 shows an X-ray diagnostics installation with an X-ray tube 1 that is operated by a high-voltage generator 2. The X-ray tube 1 emits an X-ray beam 3 that penetrates a patient 4 and, attenuated according to the transparency of the patient 4, is incident on an X-ray image transducer 5 as an X-ray image. The X-ray image transducer 5 is connected to a reproduction means that can be composed of a processing circuit 6 and a monitor 7 connected thereto for displaying the X-ray image. In a known way, the processing circuit 6 can include a calculating circuit, filter circuits, image memories and transducers, which are not shown.

A measurement transducer 8 is connected to the X-ray image transducer 5, this measurement transducer 8 being connected to the high-voltage generator 2 for controlling the X-ray dose.

Figure 2:
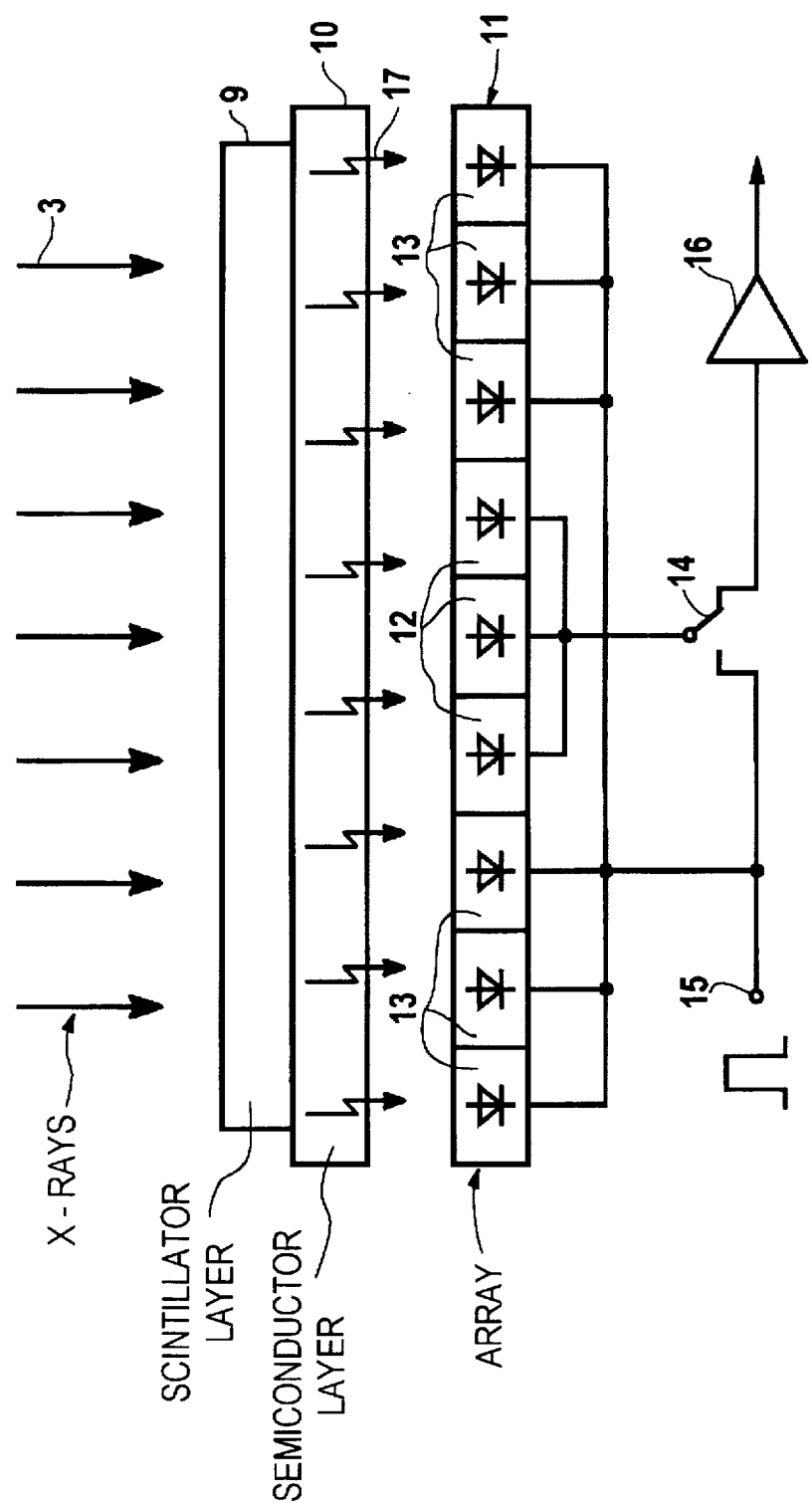
FIG. 2 illustrates the structure of the X-ray image transducer used in the inventive installation of FIG. 1.

FIG. 2 shows the X-ray transducer 5 of FIG. 1 in greater detail. The X-ray transducer 5 includes a scintillator layer 9 on which the X-ray beam 3 is incident, this being converted into a visible X-ray image according to the attenuation by the patient 4. The scintillator layer 9 can be composed of cesium iodide (CsI). A semiconductor layer 10 that is composed, for example of amorphous silicon doped with hydrogen (aSi:H), is coupled to the scintillator layer 9. The semiconductor layer 10 contains a plurality of light-sensitive pixel elements arranged in a matrix.

An array 11 of light-emitting diodes 12 and 13 arranged in a matrix for resetting residual charges of the pixel elements by illumination of the semiconductor layer 10 of the image transducer 5 is arranged behind the semiconductor layer 10, as viewed in the beam propagation direction. A first group of light-emitting diodes 12—as light-sensitive elements—is directly connected via a switch 14 and the remaining light-emitting diodes to a control terminal 15 with which the light-emitting diodes 12 and 13 are switched on, so that the semiconductor layer 10 can be illuminated in the pauses between the X-ray irradiation, and the residual charges of the pixel elements are thus reset.

A measuring amplifier 16 of the measurement transducer 8 is connected to the other contact of the switch 14. During the X-ray irradiation, the first group of lightemitting diodes 12 is connected to the measuring amplifier 16 as light-sensitive elements. Since about 15% of the light converted by the scintillator layer 9 is not absorbed by the semiconductor layer 10 and emerges at the back side thereof, this light 17 can be acquired by the light-emitting diodes 12 that are also photo-sensitive in the same color range in which they emit light. Via the measurement transducer 8, the output signal of the light-emitting diodes 12 acting as photodiodes during the X-ray pulses can be employed for shutting off the X-ray pulse when the desired X-ray dose is reached, since this voltage is proportional to the dose within the dominant.

The arrangement (configuration) of the first group of light-emitting diodes 12 is selected such that it can acquire the desired dominant region.

If each of the light-emitting diodes 12 is connected to the measuring amplifier 16 via a separate switch, then the dominant region can be arbitrarily selected. The light-emitting diodes 12 can also be combined into a plurality of groups whose arrangements (configurations) respectively have the form of the desired, possible dominants. These groups are respectively connectable to the measuring amplifier 16 via a switch.

Figure 3:
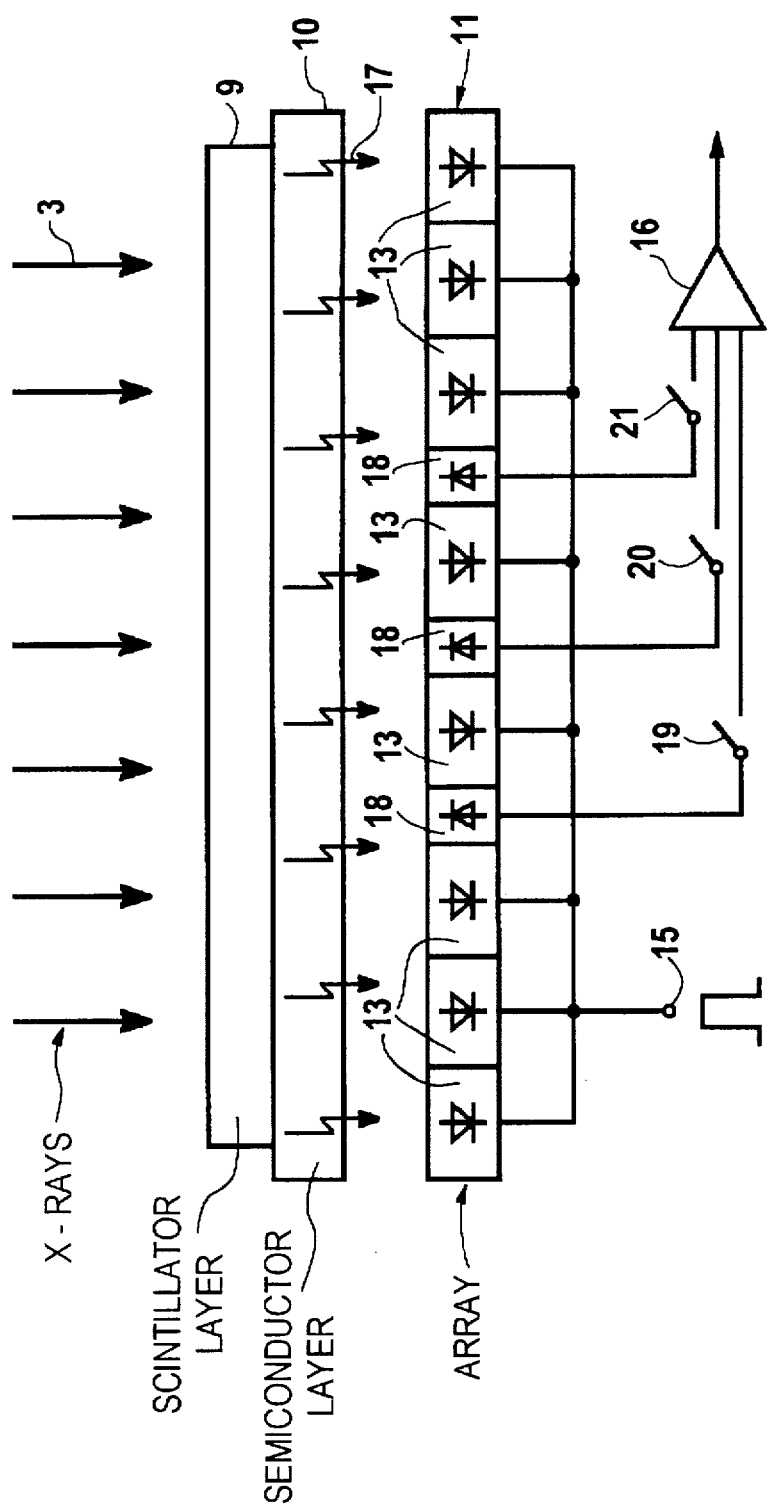
FIG. 3 illustrates a further embodiment of the structure of the x-ray image transducer used in the inventive installation of FIG. 1.

FIG. 3 shows a further possibility wherein small photodiodes 18 are arranged between the light-emitting diodes 13 as light-sensitive elements that are respectively connected to the measuring amplifier 16 via switches 19 through 21 in order to thus measure the X-ray dose. Any desired dominant can thus be selected by actuation of the individual switches 19 through 21, however, individual groups can also be combined and separately connected as group or groups can be combined as well.

Although modifications and changes may be suggested by those skilled in the art, it is the intention of the inventor to embody within the patent warranted hereon all changes and modifications as reasonably and properly come within the scope of the inventor's contribution to the art.

I claim:

1. An X-ray diagnostic installation comprising:

a high-voltage generator;

an X-ray tube connected to said high-voltage generator for emitting an X-ray beam;

an X-ray image transducer, on which said X-ray beam is incident, said X-ray image transducer having a scintillator layer, a semiconductor layer having a plurality of light-sensitive pixel elements arranged in a matrix, and an array of light-sensitive elements arranged in a matrix disposed behind said semiconductor layer in a direction of propagation of said X-ray beam;

means for driving said array of light-sensitive elements for operating at least a first portion of said light-sensitive elements as an illumination source for resetting residual charges of said pixel elements and for operating at least a second portion of said light-sensitive elements as a detector for acquiring an X-ray dose and for emitting a signal representative of said X-ray dose; and measurement transducer means, supplied with said signal, for controlling said high-voltage generator dependent on said signal.

2. An X-ray diagnostic installation as claimed in claim 1 wherein said light sensitive elements in said array comprise light-emitting diodes, and wherein said X-ray image transducer further comprises means for connecting individual ones of said light-emitting diodes to said measurement transducer means during irradiation of said X-ray transducer by said X-ray beam for forming said detector for acquiring said X-ray dose.

3. An X-ray diagnostic installation as claimed in claim 2 wherein said means for connecting comprises at least one switch for connecting at least one light-emitting diode to said measurement transducer during irradiation of said transducer by said X-ray beam and for connecting said at least one light-emitting diode to other light-emitting diodes in said array for resetting residual charges of said pixel elements.

4. An X-ray diagnostic installation as claimed in claim 1 wherein said light-sensitive elements are respectively comprised of light-emitting diodes, and wherein said light-sensitive elements in said second portion are respectively comprised of photodiodes, and wherein said means for driving comprises means for connecting said photo-diodes to said measurement transducer means during irradiation of said X-ray transducer by said X-ray beam for acquiring said X-ray dose.

5. An X-ray diagnostic installation as claimed in claim 4 wherein said photodiodes are arranged in said matrix in alternation between said light-emitting diodes in a region of a dominant.

6. An X-ray diagnostic installation as claimed in claim 1 wherein said means for driving comprises a switch connecting a group of said light-sensitive elements in said array to said measurement transducer means during irradiation of said X-ray transducer by said X-ray beam and for connecting said group of light-sensitive elements to all remaining light-sensitive elements in said array for resetting residual charges.

7. An X-ray diagnostic installation as claimed in claim 1 wherein said means for driving comprise a plurality of switches respectively connected to said light-sensitive elements in said second portion and in means for selectively closing individual switches in said plurality of switches for connecting selected light-sensitive elements to said measurement transducer means for forming a dominant having a selected shape.

8. An X-ray diagnostic installation as claimed in claim 1 wherein said means for driving comprise a plurality of switch groups, each switch group comprising a plurality of switches with the switches in each group being respectively connected to light-sensitive elements in said second portion of said array, each switch group having light-sensitive elements of said second portion of said array connected thereto in respectively different configurations corresponding to differently shaped dominance, and said means for driving comprising means for connecting a switch group to said measurement transducer means corresponding to a selected dominant shape.

9. An X-ray diagnostic installation as claimed in claim 1 wherein said image transducer comprises an aSi:H detector.

* * * * *